(12) United States Patent
Gonda

(10) Patent No.: US 6,349,719 B2
(45) Date of Patent: *Feb. 26, 2002

(54) FORMULATION AND DEVICES FOR MONITORING THE EFFICACY OF THE DELIVERY OF AEROSOLS

(75) Inventor: Igor Gonda, San Francisco, CA (US)

(73) Assignee: Aradigm Corporation, Hayward, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/795,025

(22) Filed: Feb. 26, 2001

Related U.S. Application Data

(63) Continuation of application No. 09/012,857, filed on Jan. 22, 1998, now Pat. No. 6,192,882, which is a continuation-in-part of application No. 08/804,041, filed on Feb. 24, 1997, now Pat. No. 5,829,435.

(51) Int. Cl.$^7$ ............................................... A61M 11/00
(52) U.S. Cl. .............................. 128/200.14; 128/204.23
(58) Field of Search ...................... 128/200.14, 203.12, 128/203.23, 204.23

(56) References Cited

U.S. PATENT DOCUMENTS

| | | |
|---|---|---|
| 4,242,354 A | 12/1980 | Bolasco |
| 4,649,911 A | 3/1987 | Knight et al. |
| 4,706,683 A | 11/1987 | Chilton et al. |
| 4,740,475 A | 4/1988 | Paul |
| 5,011,286 A | 4/1991 | Petralli |
| 5,404,871 A | 4/1995 | Goodman et al. |
| 5,458,135 A | 10/1995 | Patton et al. |
| 5,474,759 A | 12/1995 | Fassberg et al. |
| 5,507,277 A | 4/1996 | Rubsamen et al. |
| 5,518,902 A | 5/1996 | Ozaki et al. |
| 5,522,385 A | 6/1996 | Lloyd et al. |
| 5,527,817 A | 6/1996 | Baker et al. |
| 5,541,210 A | 7/1996 | Cupps et al. |
| 5,544,646 A | 8/1996 | Lloyd et al. |
| 5,607,662 A | 3/1997 | Baskeyfield et al. |
| 5,608,647 A | 3/1997 | Rubsamen et al. |
| 5,619,984 A | 4/1997 | Hodson et al. |
| 5,642,728 A | 7/1997 | Andersson et al. |
| 5,672,581 A | 9/1997 | Rubsamen et al. |
| 5,829,435 A | 11/1998 | Rubsamen et al. |
| 5,888,477 A | 3/1999 | Gonda et al. |
| 6,192,882 B1 * | 2/2001 | Gonda ................... 128/203.21 |

FOREIGN PATENT DOCUMENTS

WO     WO 94/27653     12/1994

* cited by examiner

Primary Examiner—Mital Patel
(74) Attorney, Agent, or Firm—Karl Bozicevic; Bozicevic, Field & Francis LLP

(57) ABSTRACT

Aerosolizable formulations are disclosed comprised of a pharmaceutically acceptable carrier, a pharmaceutically active drug or detectably labeled compound and a compound which is recognized by its distinct color, taste and/or smell even when present in a small amount and a low concentration. Examples of such compounds include menthol, peppermint, cinnamon and vanilla flavors and water soluble dyes. The compounds can be designed so that they are only detectable by a specific area of the tongue or seen under a certain wavelength of light. The degree of detection of the color, taste or smell of the compound is an indication of the degree of success in the delivery of an aerosolized formulation to a patient. The formulation is preferably delivered from a device which monitors and records information relating to the patient's respiratory movement and also scans and analyzes the aerosol prior to inhalation. The device sends the user a visual and/or audible signal which informs the user about the character of the aerosol formed. By means of the taste and smell as well as the signal obtained from the device the user is provided with multiple indications of the efficacy of the aerosolized dose delivered.

13 Claims, 3 Drawing Sheets

FORMULATION AND DEVICES FOR MONITORING THE EFFICACY OF THE DELIVERY OF AEROSOLS

CROSS REFERENCES

This application is a continuation of earlier filed U.S. patent application Ser. No. 09/012,857 filed Jan. 22, 1998, now issued U.S. Pat. No. 6,192,882 B1 on Feb. 27, 2001 which application is a CIP to U.S. patent application Ser. No. 08/804,041, filed Feb. 24, 1997, now issued U.S. Pat. No. 5,829,435 which applications are incorporated herein by reference and to which applications we claim priority under 35 U.S.C. §120.

FIELD OF THE INVENTION

The invention relates to the field of aerosol formulations, packaging for dispersing such and devices for the delivery of aerosols. More specifically, the invention relates to formulations containing additives with distinct tastes, colors, smells and/or emmitors of gamma radiation and aerosol devices with sensors designed to monitor the formation and delivery of such aerosols.

BACKGROUND OF THE INVENTION

Aerosolizing formulations for inhalation has been considered as a convenient alternative to injection for decades. This alternative to injections is particularly interesting for drugs which cannot be delivered orally, e.g. insulin. Although most compounds will effectively move from the lungs into the circulatory system there is considerable unpredictability in how much aerosolized formulation reaches the areas of the lungs where the material can move into the circulatory system. This results in inefficiency and unpredictability of dosing. A number of devices have been proposed for improving the efficiency of aerosol delivery, monitoring patients and teaching patients to correctly use delivery devices. The present invention makes it easy for the user to directly monitor aspects of aerosol delivery in a manner which improves repeatability of dosing.

SUMMARY OF THE INVENTION

Aerosolizable formulations are disclosed comprising a pharmaceutically acceptable carrier, a pharmaceutically active drug or detectably labeled compound and a sensory compound which is recognized by its distinct taste, color and/or smell even when present in a small amount and a low concentration. Examples of such sensory compounds include menthol, peppermint, cinnamon and vanilla flavors as well as dyes which have colors which contrast with the color of the inner mouth and throat. The compounds can be designed so that they are detectable by a specific area of the tongue, i.e., the specific area which preferentially detects sweet, salty, sour or bitter flavors. The degree of detection of the taste or smell of the compound and the perceived taste or smell is an indication of the degree of success in the delivery of an aerosolized formulation to a patient, with little or no taste detection indicating delivery predominately to the lung. When a color component is included such as a dark blue or purple dye the lack of any such coloring inside the mouth or throat after delivery is an indication of a successful delivery. The formulation is preferably delivered from a device which monitors and records information relating to the patient's respiratory movement and also scans and analyzes the aerosol prior to inhalation. The device sends the user a visual and/or audible signal which informs the user about the character of the aerosol formed. By means of the color, taste and smell sensed as well as the signal obtained from the device the user is provided with multiple indications of the efficacy of the aerosolized dose delivered. These indications assist the user in improving delivery techniques, and in analyzing the effectiveness of a given delivery procedure after it has been performed thereby improving repeatability of dosing. The sensory compounds may be used together, separately or in any combination and may be used with or without a device which monitors one or more respiratory parameters.

An object of the invention is to provide an aerosol formulation which comprises a sensory compound having a color, taste and/or smell which provides the user with an indication of the efficacy of aerosol delivery.

Another object is to provide formulations which comprise compounds which emit radiation which is detectable by counters or cameras which detect the particular radiation emitted e.g. gamma emissions.

Another object is to provide a device for aerosolizing formulations which monitors the physical characteristics of aerosols created (e.g. particle size) and provides the user with an audio and/or visual signal which indicates the character of the aerosol.

Another object is to provide a formulation with a taste which is particularly noted on contact with a particular area of the tongue thereby allowing a user to determine how a particular aerosolized burst was misdirected.

Another object is to provide a system of delivery of aerosols which causes the patient to become accustomed to certain sensory perceptions during a normal delivery event, such that an abnormal delivery will be perceived by the patient as different.

An advantage of the invention is that it provides a device with a formulation which uses the electronic sensory components available in the device along with the users own senses to monitor the delivery of aerosolized doses.

A feature of a formulation of the invention is that it has a distinct detectable color, taste and/or smell.

Another feature of the invention is that an optical scanner is used to characterize aerosols formed.

An advantage of the invention is that the user is quickly and conveniently provided with information indicative of the efficacy of delivery of an aerosolized dose.

These and other objects, advantages and features of the present invention will become apparent to those skilled in the art upon reading this disclosure in combination with drawings wherein like numerals refer to like components throughout.

DESCRIPTION OF THE PREFERRED EMBODIMENTS

Figure 1:
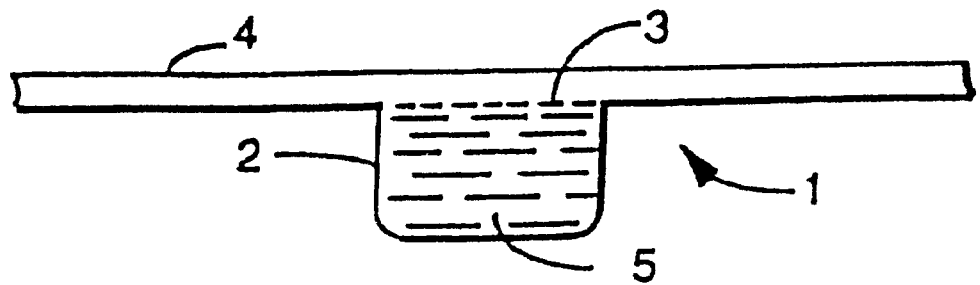
FIG. 1 is a schematic, cross-sectional view of an embodiment of a sample container.

Before the present formulation, device and method of detecting particles is described, it is to be understood that this invention is not limited to the particular methodology, devices, containers and formulations described, as such methods, devices, containers and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an, " and "the" include plural referents unless the context clearly dictates otherwise. Thus, for example, reference to "a sensory compound" includes mixtures of different sensory compounds, reference to "an assay" includes one or more assays, and reference to "the method of detection" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

The publications discussed herein are provided solely for their stated disclosure prior to the filing date of the present application. Nothing herein is to be construed as an admission that the invention is not entitled to antedate such publications by virtue of prior invention. Further, the actual date of publication may be different from that stated on the publication and as such may require independent verification of the actual publication dates.

Definitions

The term "sensory compound" is used here to encompass any compound or group of compounds which provide any or all of a distinct color, taste or smell to the human eye, tongue or nose. The sensory compound relating to taste preferably has a distinct taste which is readily detected by the human tongue and preferable by taste buds on a particular area of the tongue thereby providing a distinct sour, sweet, salty or bitter taste even when present in a small amount and/or in a low concentration. A sensory color compound preferably has a color which distinctly contrasts with the color of the inside of the mouth and tongue. The color, taste and/or smell of the sensory is preferably sufficiently different from the color, taste or smell of the carrier or active compound present that human eyes, taste buds and olfactory senses can readily determine the difference between them. The sensory compound may be different from the carrier or active compound by having a distinctly stronger taste, smell or color, e.g., have the same basic taste, color or smell but have such in a form which is 5 to 10 more time concentrated as compared to the drug and or carrier of the formulation.

The term "formulation" is used to describe any mixture, solution, suspension or the like comprising a sensory compound. The formulation is preferably further comprised of an active ingredient and a carrier and more preferably is a liquid that has physical properties such that when the formulation is moved through a porous membrane the formulation is aerosolized into particles which are inhaled into the lungs of a patient and preferably reach the circulatory system. The active ingredient may be any pharmaceutically active drug or detectably labeled compound. The carrier may be any pharmaceutically acceptable material and is preferably a flowable liquid which is compatible with the sensory compound and the active agent. Formulations are preferably solutions, e.g., aqueous solutions, ethanolic solutions, aqueous/ethanolic solutions, saline solutions, colloidal suspensions and microcrystalline suspensions. Formulations can be solutions or suspensions of sensory compounds and/or drugs in the above mentioned liquids or in the case of a metered dose inhaler a low boiling point propellant—see U.S. Pat. Nos. 5,404,871; and 5,608,647. Other formulations can be in the form of dry powders of sensory compounds with or without drugs and carriers see U.S. Pat. No. 5,458,135.

The term "carrier" shall mean a pharmaceutically acceptable excipient material which a sensory compound, an active ingredient such as a drug, a diagnostic agent or a gene vector is mixed with, suspended or dissolved in. The carrier is preferably a flowable liquid. Useful carriers do not adversely interact with the sensory compound, drug, diagnostic or gene therapy and have properties which allow for the formation of aerosolized particles preferably particles having a diameter in the range of 1.0 to 8.0 microns when a formulation comprising the sensory compound, carrier and active ingredient is forced through pores having a diameter of 0.5 to 4.0 microns. Carriers include water, ethanol, saline solutions and mixtures thereof with pure water being preferred. Other carriers can be used provided that they can be formulated to create a suitable aerosol and do not adversely effect the particular sensory compound, active component or human lung tissue. Dry powder carriers can aid in separation of the particles.

The term "active compound" means a compound which is either a pharmaceutically active drug, or a detectably labeled compound. In turn, a "pharmaceutically active drug" shall be interpreted to mean any pharmaceutically effective compound used in the treatment of disease. A "detectably labeled compound" includes compounds which are radioactively labeled see U.S. Pat. application Ser. No. 08/789,551 Re: detectable labels.

The terms "electronic particle sensing device" and "electronic detection system" refer to a device or other means for measuring and counting particles present in an aerosol mist.

The term "reporting means" is used herein to indicate a means by which information obtained from a monitoring device such as an electronic particle sensing device or a device which monitors and records information relating to the patient's respiratory movement, may be provided to the user.

The terms "aerosol", "aerosol bolus", and the like, are used interchangeably herein to describe a volume of air greater than 50 ml and less than 4 liters which has suspended within it particles of a formulation wherein the particles have a diameter in the range of 0.5 to 8.0 microns, preferably 1 to 3 microns, and preferably the total volume of formulation is from 10 $\mu$l to 10,000 $\mu$l. About 10 $\mu$l of particles having a diameter of about 1 to 3 microns are present in a volume of about 50 ml to 2 liters, preferably 100 ml to 1,000 ml.

In referring to particle diameter, the diameter measurement given is the "aerodynamic diameter" measurement which is the diameter of a sphere of unit density that has the same terminal sedimentation velocity in air under normal atmospheric conditions as the particle in question. This is pointed out in that it is difficult to accurately measure the diameter of small particles using current technology and the shape may be continually changing. Thus, the diameter of one particle of material of a given density will be said to have the same diameter as another particle of the same material if the two particles have the same terminal sedimentation velocity in air under the same conditions.

The terms "air", "particle free air", "aerosol free air," and the like, are used interchangeably herein to describe a volume of air which is substantially free of other material and, in particular, free of particles intentionally added such as particles of formulation. The term means that the air does not include particles of formulation which have been intentionally added but is not intended to imply that the normal surrounding air has been filtered or treated to remove all particles although filtering can take place.

The term "measuring" describes an event whereby the (1) total lung capacity, (2) inspiratory flow rate or (3) inspiratory volume of the patient is measured and/or calculated and the information used in order to determine an optimal point in the inspiratory cycle at which to release an aerosol and/or a particle free volume of air. An actual measurement of both rate and volume may be made or the rate can be directly measured and the volume calculated based on the measured rate. The total lung capacity can be measured or calculated based on the patient's height, sex and age. It is also preferable to continue measuring inspiratory flow during and after aerosol delivery and to record inspiratory flow rate and volume before, during and after the release of formulation. Such reading makes it possible to determine if formulation was properly delivered to the patient.

The term "monitoring" event shall comprise detecting taste and/or smell and determining the character of an aerosol such as the size, number and speed of the particles in the aerosol, further, monitoring may comprise measuring lung functions such as inspiratory flow, inspiratory flow rate, and/or inspiratory volume so that a patient's lung function as defined herein, can be evaluated during before and/or after delivery thereby making it possible to evaluate the effect of formulation such as respiratory drug delivery on the patient's lung function.

The term "inspiratory flow rate" shall mean a value of air flow rate determined, calculated or measured based on the speed of the air passing a given point in a measuring device assuming atmospheric pressure ±5% and a temperature in the range of about 10° C. to 40° C.

The term "inspiratory flow" shall be interpreted to mean a value of air flow calculated based on the speed of the air passing a given point along with the volume of the air that has passed that point with the volume calculation being based on integration of the flow rate data and assuming atmospheric pressure, ±5% and temperature in the range of about 10° C. to about 40° C.

The term "inspiratory volume" shall mean a determined, measured or calculated volume of air passing a given point into the lungs of a patient assuming atmospheric pressure ±5% and a temperature in the range of 10° C. to 40° C.

The terms "lung function" and "pulmonary function" are used interchangeably and shall be interpreted to mean physically measurable operations of a lung including but not limited to (1) inspiratory and (2) expiratory flow rates as well as (3) lung volume, i.e., total lung capacity. Methods of quantitatively determining pulmonary function are used to measure lung function. Quantitative determination of pulmonary function may be important when delivering any formulation and in particular respiratory drugs in order to direct the aerosol to a specific area of the lung and to determine effectiveness. Methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second ($FEV_1$), allows bronchoconstriction to be quantitatively evaluated. A problem with forced vital capacity determination is that the forced vital capacity maneuver (i.e. forced exhalation from maximum inspiration to maximum expiration) is largely technique dependent. In other words, a given patient may produce different FVC values during a sequence of consecutive FVC maneuvers. The FEF 25–75 or forced expiratory flow determined over the mid-portion of a forced exhalation maneuver tends to be less technique dependent than the FVC. Similarly, the $FEV_1$ tends to be less technique dependent than FVC. In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest air flow rate in liters per minute during a forced maximal exhalation, is well correlated with overall pulmonary function in a patient with asthma and other respiratory diseases. The present invention carries out treatment by administering formulation in a delivery event and monitoring lung function in a monitoring event. A series of such events may be carried out and repeated over time to determine if lung (see U.S. Pat. No. 5,404,871) function is improved.

Each of the parameters discussed above is measured during quantitative spirometry. A patient's individual performance can be compared against his personal best data, individual indices can be compared with each other for an individual patient (e.g. $FEV_1$ divided by FVC, producing a dimensionless index useful in assessing the severity of acute asthma symptoms), or each of these indices can be compared against an expected value. Expected values for indices derived from quantitative spirometry are calculated as a function of the patient's sex, height, weight and age. For instance, standards exist for the calculation of expected indices and these are frequently reported along with the actual parameters derived for an individual patient during a monitoring event such as a quantitative spirometry test.

The terms "particles", "aerosolized particles" and "aerosolized particles of formulation" shall mean particles of formulation comprised of any sensory compound and preferably an active ingredient and a carrier, (e.g., a pharmaceutically active respiratory drug and carrier). Particles of a liquid formulation are formed upon forcing the formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs. Preferably, the particles have a size in the range of 0.5 micron to about 8 microns, preferably 1 to 3 microns having been created by being forced through the pores of a flexible porous membrane which pores have a diameter in the range of about 0.25 micron to about 6.0 microns (note that a pore with a diameter of 4.0 microns will produce a particle with a diameter of about 8.0 microns which particle can be reduced to any size (e.g., 3.0 or less) via evaporation—the pores being present on the membrane in a density of about ten to 10,000 pores over an area in size of from about 1 sq. millimeter to about 1 sq. centimeter. As indicated above, particle diameter is an aerodynamic diameter.

General Overview

A formulation of the invention comprises a sensory compound and preferably a pharmaceutically acceptable carrier having an active compound dispersed or dissolved therein. The active compound is a pharmaceutically active drug or a radioactive labeled compound. The sensory compound exhibits one or more distinctive tastes and/or smells which are preferably different from and stronger than that of the carrier, active drug, or labeled compound.

When properly administered, an aerosolized burst of formulation only contacts certain surfaces in the respiratory tract. However, if the aerosol is misdirected, e.g., at the tongue, the formulation (or a portion thereof) does not reach the lungs. The user may not know that the formulation was not delivered properly and thereby remain inadequately treated.

Formulations of the invention are detected by the user due to a sensory compound which preferably has a distinct taste or tastes and more preferably has a distinct taste or tastes which are sensed by a particular area of the tongue. A human tongue detects different types of tastes, i.e. sweet, bitter, sour, on different areas of the tongue. Thus, if an aerosolized burst is misdirected against the tongue the user will be able to detect the mistake via taste. The user may then correct the error by re-directing the spray (or moving the tongue) and re-administer the aerosolized dose.

In addition to under dosing by misdirecting an aerosolized burst an error may take place due to a malfunction of the device. The malfunction could result in (1) no aerosol being released, (2) inadequate aerosol being released, or (3) aerosol being released with particles having a size distribution which is incorrect for the type of pulmonary drug delivery desired. Complete failure to deliver aerosol may be detected in a number of ways. One way is to include a sensory compound in the formulation which has a distinct smell. If the user does not detect the smell after activating the device then the user can assume no aerosol was released. The user can then check the electronic reporting system of the device to see if aerosol was actually released. The reporting system of the device preferably also detects if and how many particles were released but whether the particles formed were of the correct size.

Color, Taste and Smell as a Means of Monitoring Aerosol Delivery

Humans are able to perceive and recognize many different tastes, all of which can be classified into four primary types: sweet, salty, sour and bitter. Taste is mediated by sensory receptors known as taste buds, which are located in groups on epithelial structures known as papillae. Most taste buds are on the tongue, however, some are also present on the palate, pharynx, larynx, and upper esophagus. The amount of taste buds and their sensitivity varies somewhat between individuals. Thus, each user of the present invention may require some learning or adjustment period to fully utilize the invention.

In one method of the invention the patient first delivers doses in a controlled environment to learn how to correctly use the device and comes to know the type and intensity of taste that is sensed for a correct delivery. Once a pattern is established the patient can notice the difference for an incorrect delivery.

While individual taste buds are not entirely specific for a particular primary taste, each responds optimally to one kind and less well to the others. The various types of taste buds are distributed on the tongue's surface such that different regions are more highly sensitive to one particular taste then to the others. Thus, the tip of the tongue is especially sensitive to sweet, the sides proximate to the tip to salty, the posterior edges to sour, and the posterior surface to bitter.

By including a sensory compound that has a distinctive taste in the aerosol formulation, the user is provided with a means for indicating the degree of success in delivery of that formulation, with little or no taste sensation indicating delivery predominantly to the lungs. Further, the inclusion of a sensory compound which is sensed by a particular area of the tongue allows a user to determine whether and how a particular aerosolized burst was misdirected, (or how the tongue was improperly positioned) and thereby permits the user to redirect the aerosol flow (or reposition the tongue) and re-administer an additional dose.

Similarly, the human olfactory system is capable of recognizing a myriad of different odors. Although difficult to classify, there are at least seven primary ones: camphoraceous, musk, floral, peppermint, ethereal, pungent and putrid.

Olfactory receptor cells are themselves primary afferent neurons. Each olfactory receptor cell has an apical process with cilia that extends into a layer of mucus located at the olfactory mucosa, a specialized area present in each nasal mucosa. When chemical substances capable of eliciting an olfactory response are inhaled, they become dissolved in the mucus layer and bind to receptor molecules on the cells' cilia. Binding stimulates the receptor cell and causes a signal to be carried along that cell's axon to the brain, where it is processed and ultimately perceived as a particular scent.

By including a sensory compound that has a distinctive smell in the aerosol formulation, the user is provided with a means for indicating whether the device has malfunctioned and failed to deliver aerosol. If no smell is detected after activating the device, then the user can assume that the device has malfunctioned and has failed to release any aerosol. The user can then check the electronic reporting system of the device to see if aerosol was actually released, and additionally, to see whether the particles formed were of the correct size.

Color can be used alone or in combination with compounds having a distinct taste or smell. The color can be any color but is preferably a color easily recognized by human eyes and preferably sharply distinct from the color of the tongue and the inside of the mouth. The color is preferably a water soluble dye such as deep blue or purple such as conventional food coloring The color component may inherently include a distinct taste and/or smell, just as a taste component may be designed to have a distinct color or smell.

Aerosol Formulation

The aerosol formulations of the present invention are comprised of a pharmaceutically acceptable carrier, an active compound selected from the group consisting of pharmaceutically active drug and a detectably labeled compound, and one or more sensory compounds having any or all of a distinct color, taste and smell.

With respect to sensory compounds having a distinctive taste, a wide variety of compounds are suitable. Generally, such compounds, are those with a distinct, sweet, sour, bitter or salty taste or those with a floral or peppermint smell. Examples include saline, sucrose, and citrus solutions for taste and peppermint flavor for smell and taste.

With respect to sensory compounds having a distinctive smell, there is also a wide variety of compounds which might be employed. Generally, compounds suitable for use in the present invention are those with a pleasant smell. Examples include floral perfumes, menthol, peppermint, cinnamon, and vanilla. Especially preferred are the compounds menthol, peppermint, cinnamon and vanilla.

With respect of a compound with a distinct color any color agent can be used but those that are water soluble are preferred. Bright blues, greens and purples as well as black provide a stark contrast with the color of the mouth and as such are preferred. It is also possible to use coloring agents which are fluorescent including agents which fluoresce when exposed to certain wavelengths of light.

With respect to active compounds it is possible to deliver a wide range of compounds using the present invention. For example, drugs included within the container could be anti-inflammatory drugs, insulin, analgesics, bronchodilators, antibiotics, enzymes, steroids or anticholinergics.

The active compound can also be variety of detectably labeled compounds, including those that are radioactively labeled, such as are described in U.S. application Ser. No. 08/597,084 filed Feb. 5, 1996.

Active compounds may be stored in and/or released from a container of any desired size. In most cases the size of the container is not directly related to the amount of active compound being delivered in that most formulations include relatively large amounts of carrier. Accordingly, a given size container could include a wide range of different doses by varying the concentration of the active compound.

Carriers: A wide variety of pharmaceutically acceptable carriers are known which are suitable for use in the formulation of the present invention. Such carriers include alcohol, (e.g., ethanol with or without water) water or a saline solution. Pure water is preferred. If the formulation is a dry powder a carrier may or may not be used. If the formulation is for use in the metered dose inhaler (MDI) device the carrier will be a low boiling point propellant.

Viscosity of formulation: The drug formulation may be a low viscosity liquid formulation. Generally, the viscosity of the drug by itself or in combination with a carrier is not of particular importance except to note that the formulation must have characteristics such that the formulation can be aerosolized to form aerosol mist, the aerosols having a particle size in the range of about 0.5 to 12 microns, preferably 1–4 microns.

Formulation Containers

FIG. 1 is a cross-sectional view of a formulation container 1 which is shaped by a collapsible wall 2. The container 1 has an opening covered by a flexible porous membrane 3 which is covered by a removable layer 4. The layer 4 may be labeled "sweet", "sour", "peppermint", "blue", "green", etc. to identify the sensory compound. The membrane 3 may be rigid and protrude upward in a convex configuration away from the formulation 5. When the layer 4 is removed the wall 2 can be collapsed thereby forcing the formulation 5 against the flexible porous membrane 3 which will then protrude outward in a convex shape. In an alternate collapsible configuration not shown the bottom wall could be made to slide like a piston and fit tight against cylindrical walls thereby forcing the contents out. Although a container is generally empty after one aerosol burst is created the container can be designed so that multiple (e.g., 2–10) bursts can be extruded. However, the burst must be extruded over a short period e.g., less than one hour to avoid contamination or clogging problems. After use the container is discarded, see U.S. Pat. No. 5,544,646 issued Aug. 13, 1996.

Figure 2:
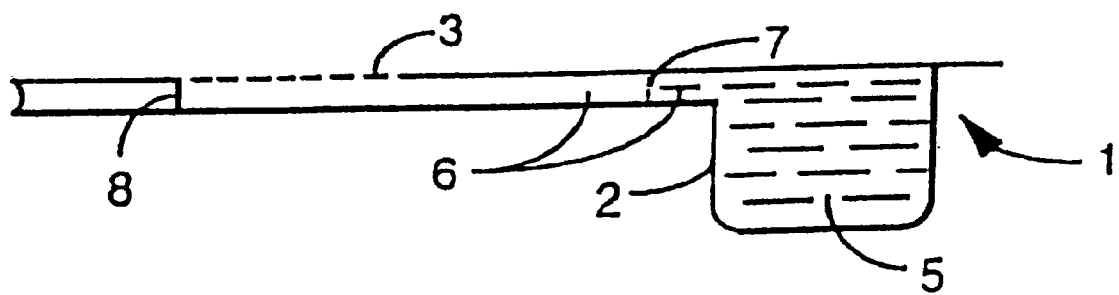
FIG. 2 is a schematic cross-sectional view of another embodiment of a sample container.

FIG. 2 is a cross-sectional view of a more preferred embodiment of a formulation container 1. The container is shaped by a collapsible wall 2. The container 1 includes an opening which leads to an open channel 6 which channel 6 includes an abutment 7 which is opened upon the application of force created by formulation 5 being forced from the container. When the abutment 7 is opened the formulation 5 flows to an area adjacent to the flexible porous membrane 3 and is prevented from flowing further in the channel 6 by a non-breakable abutment 8.

Figure 4:
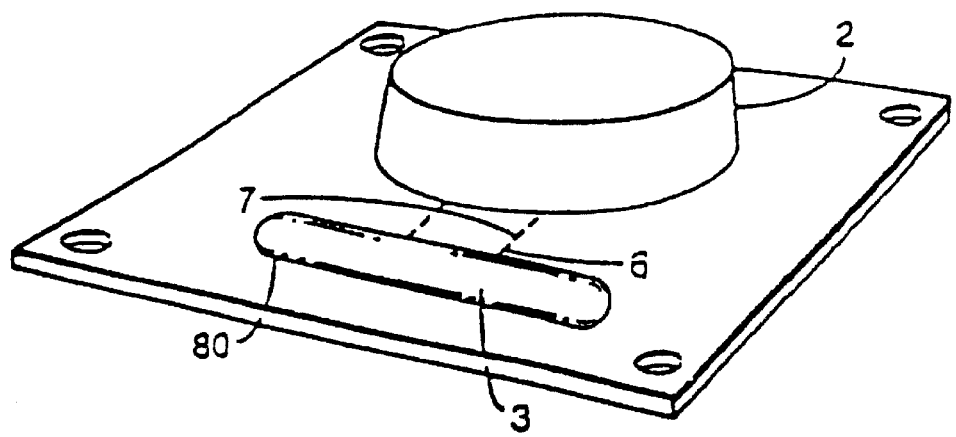
FIG. 4 is a perspective view of the sample container.

FIG. 4 is a perspective view of a preferred embodiment of the container depicted in FIGS. 1 and 2.

Figure 5:
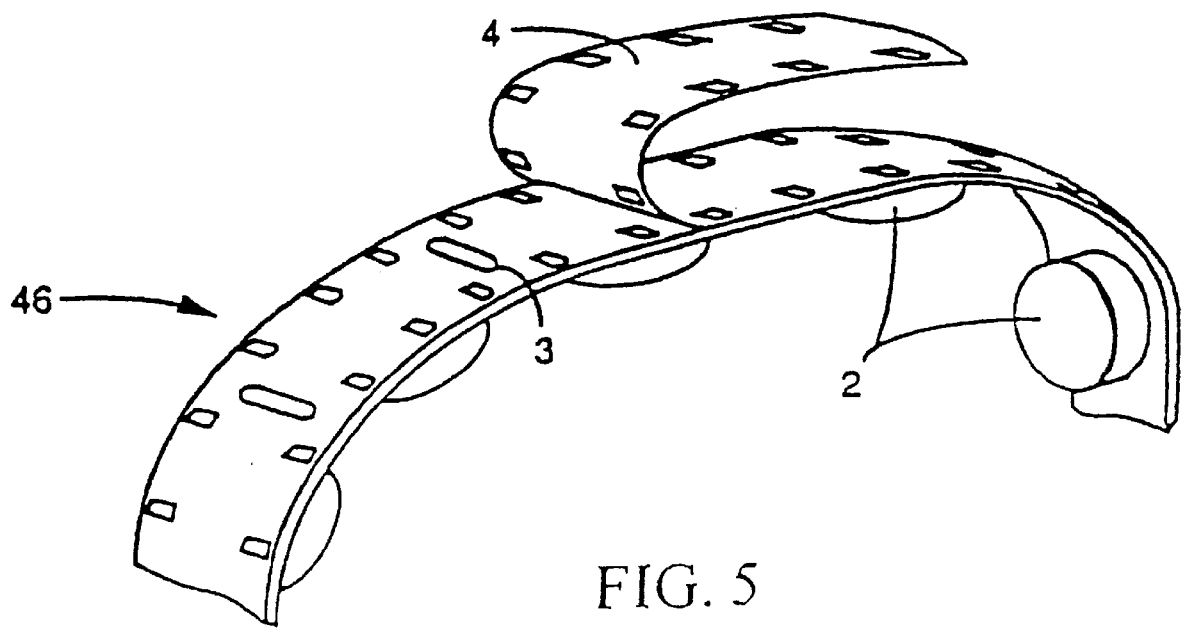
FIG. 5 is a perspective view of a plurality of sample containers linked together.

The disposable package 46 is shown in FIG. 5. The package is comprised of a plurality of disposable containers 1, shown in detail in FIGS. 1,2 and 4. Each container 1 includes a formulation 5 and is covered by the porous membrane 3. Formulations comprising the sensory compound may be stored in and/or released from a container of any desired size. A number of containers may be connected together to form a package 46 as shown in FIG. 5. The package 46 is in the form of an elongated tape but can be in any configuration, e.g., circular, square, rectangular, etc.

Formulation containers 1 or packages 46 may include indices providing information such as the contents of the formulation (e.g., the taste or smell of the sensory compound) or other pertinent information. Thus, information as to the particular type and concentration of sensory compound, drug or detectably labeled compound present in the formulation may be indicated on the formulation container. Such indices may be in the form of visually perceivable symbols such as numbers or letters; alternatively, they may be in the form of electronically, magnetically or optically recorded information perceivable by electronic means, which means may be separate or may be part of the delivery device. The indices are preferably in the form of a resistor with a set resistance value specifically set to correspond to a specific formulation with a given sensory compound, drug, and carrier.

Delivery Device

It is important to note that a variety of devices can be used in order to carry out the methodology of the present invention. However, the device must be capable of aerosolizing formulation in a container, and preferably includes both a means of detecting the presence and size of the aerosol particles being released, and a means for monitoring and recording information relating to the patient's respiratory movement. An example of such a device is disclosed in U.S. Pat. No. 5,522,385 and U.S. patent application Ser. Nos. 08/534,786 filed Sep. 27, 1995, and 08/804,041 filed Feb. 24, 1997.

Figure 3:
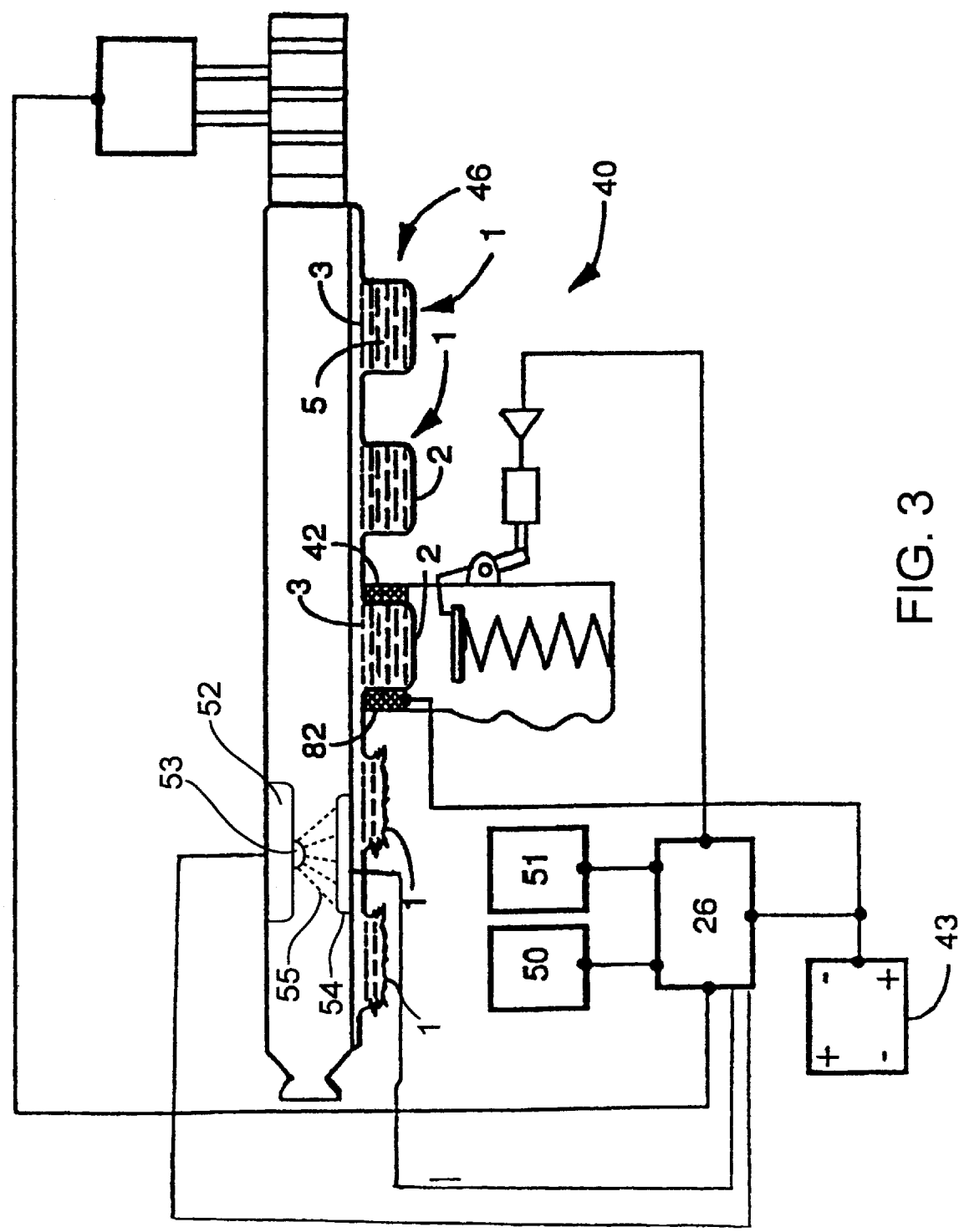
FIG. 3 is a schematic view of a delivery device which includes a particle detection device.

A plan view of such a drug delivery device is shown in FIG. 3. The device 40 is loaded and operates with a package 46 of multiple formulation containers.

The device 40 pictured in FIG. 3 is a hand-held, portable delivery deice which is comprised of (a) a device for holding a disposable package 46 with at least one but preferably a number of containers 1, and (b) a mechanical mechanism for forcing the contents of a container (on the package) through a porous membrane. Preferably, the device further comprises (c) an electronic particle sensing device 52 for sensing both the presence and size of aerosol particles, (d) a means 50 for monitoring and recording information relating to the patient's respiratory movement, and (e) reporting means 51 for providing the user with the information obtained via components (c) and (d).

Electronic Detection System: The electronic detection system 52 can include an energy or light source 53 and a receiver 54 which detects energy 55 sent from the source 53 and detects interruption of that energy when deflected, as by a particle in the mouth piece tube 30.

Systems and devices which measure, count and analyze particles in a fluid are known. Such devices are employed, for example, by semiconductor wafer manufacturers to monitor the extent of airborne particulate matter in a clean room. Pharmaceutical manufacturers employ such devices for the detection and control of foreign particles. To a lesser extent of accuracy, smoke detectors also measure particle concentration. Such devices and variations thereof can be used in connection with the present invention to determine (1) if an aerosol of any sort is created at the desired point; and (2) the character of the aerosol in terms such as the number and size of the particles present per unit volume.

One method of particle detection is the light blockage particle counting, or light obscuration, method. Light obscuration sensors work on the principle of the casting of a shadow onto a photo detector as a flow of particle-laden fluid is directed through a light beam generated by an incandescent lamp.

A more sensitive method is the light scattering method. As a particle passes through a light beam, the particle scatters light. The amount of scattered light is a function of the particle size, the wavelength and intensity of the incident light, and the difference between the light scattering properties of the particle and the surrounding medium. A laser source may be used to generate the light beam and the scattered light is sensed by a detector which provides readable signals indicative of particle size.

The device is preferably calibrated against a standard which makes it possible for the device to determine if the reading is within a satisfactory range for the results being sought. If readings outside a given range are obtained the device signals the user of such—indicating an incorrect drug delivery event. The flow measurement sensor can detect the velocity of the particles in addition to their size and particle density. All of the parameters can be measured against a standard and the user can be advised if a reading is below or above a standard preferred range.

It is an object of the present invention to provide an apparatus for detecting particles (their, speed, size velocity etc.) which is simple, inexpensive and small in size so that it can be used in a hand-held inhalation device. The devices as described herein could be equipped with different types of particle detection and measuring devices such as devices for particle detection disclosed in U.S. Pat. No. 5,011,286, issued Apr. 30, 1991 to Petralli (incorporated herein by reference).

Such devices and method generally require (A) a light source, (B) a photo detector, (C) a means for interpreting the photo detector signals and (D) the presence of particles which absorb or deflect light.

Device for holding disposable package: The device for holding the disposable package may be nothing more than a narrow opening created between two outwardly extending bars 42 and 82 or may include additional components for moving new packages into position such as one or more wheels, sprockets or rollers notably mounted on the end(s) of such bars. The rollers may be spring mounted so as to provide constant pressure against the surface(s) of the package. The device may also include a transport mechanism which may include providing drive power to the roller(s) so that when they are rotated, they move the package from one container to the next. After the formulation in a container is aerosolized the container is discarded and a new full container brought into the aerosol release position. The power source 43 driving the roller(s) is programmed via the microprocessor 26 to rotate the rollers only enough to move the package 39 from one container 1 to the next. The power source 43 is preferably in the form of standard compact batteries including rechargeable batteries and alkaline batteries.

Method of Use

The formulation preferably includes a sensory compound having a distinctive color and taste, so as to enable the user to determine whether the aerosol has been properly generated and directed to the desired area of the respiratory tract. If the user detects the colored and flavored compound after administering an initial dose, he or she may redirect the spray away from the area of the tongue where the taste was detected, or area where color was seen, such that the subsequent dose is properly directed. Additionally or alternatively the light sensor of the device can produce a signal indicating if the aerosol was formed in the desired manner e.g. desired particle size and/or number of particle per cubic unit of space. These indications, which may be combined with smell, taste and color provide the user with information useful to obtain repeatable dosing. It is particularly advantageous to use the present invention when delivering drugs which have a narrow therapeutic window. For example, the invention can be used with the aerosolized delivery of insulin (see U.S. Pat. No. 5,672,581 and U.S. application Ser. No. 08/792,616 filed Jan. 31, 1997) and narcotics (see U.S. Pat. No. 5,507,277). The insulin may be a monomeric insulin e.g. insulin lispro.

The instant invention is shown and described herein in which is considered to be the most practical and preferred embodiments. It is recognized, however, that the departures may be made therefrom which are within the scope of the invention and that obvious modifications will occur to one skilled in the art upon reading this disclosure.

What is claimed is:

1. A method of monitoring aerosol delivery efficacy, comprising:

creating an aerosolized mist of particles 25% or more of which having a diameter in the range of from about 1 micron to about 8 microns wherein the particles are comprised of:

an active compound selected from the group consisting of pharmaceutically active drug and a radioactive labeled compound, and a sensory compound with a characteristic selected from the group consisting of a distinctive color, a distinctive taste and a distinctive smell;

inhaling the aerosolized mist through the mouth and into the lungs; and analyzing delivery efficacy to the lungs based on detected color, taste or smell.

2. The method as claimed in claim 1, wherein the active compound is a pharmaceutically active drug.

3. The method of claim 2, wherein the particles are further comprised of a pharmaceutically acceptable carrier.

4. The method of claim 3, wherein the carrier is selected from the group consisting of water, ethanol and a saline solution.

5. The method of claim 2, wherein the pharmaceutically active drug is selected from the group consisting of anti-inflammatory, insulin, an analgesic, a bronchodilator, an antibiotic, an enzyme, a steroid, and an anticholinergic.

6. The method of claim 2, wherein the pharmaceutically active drug is insulin.

7. The method of claim 2, wherein the drug is a narcotic.

8. The method of claim 2, wherein the drug is a monomeric insulin.

9. The method of claim 2, wherein the monomeric insulin is insulin lispro.

10. The method of claim 2, further comprising:
scanning the aerosolized mist with light;
analyzing the aerosolized mist based on the scan; and
providing a user with results of the analysis.

11. The method as claimed in claim 1, wherein the particles are in the form of a dry powder.

12. The method as claimed in claim 11, wherein the sensory compound has a color which distinctly contrasts with surface coloring on a tongue.

13. The method as claimed in claim 11, wherein the sensory compound has a taste detectable on a particular area of a tongue.

* * * * *